United States Patent [19]

Spievack

[11] Patent Number: 5,536,269
[45] Date of Patent: * Jul. 16, 1996

[54] BONE AND TISSUE LENGTHENING DEVICE

[75] Inventor: Alan R. Spievack, Watertown, Mass.

[73] Assignee: Genesis Orthopedics, Cambridge, Mass.

[*] Notice: The portion of the term of this patent subsequent to Sep. 27, 2011, has been disclaimed.

[21] Appl. No.: 200,073

[22] Filed: Feb. 22, 1994

Related U.S. Application Data

[63] Continuation-in-part of Ser. No. 18,820, Feb. 18, 1993, Pat. No. 5,350,379.

[51] Int. Cl.$^6$ ................................................. A61B 17/72
[52] U.S. Cl. ................................................. 606/63; 606/64
[58] Field of Search ................................. 606/63, 68, 60, 606/62, 64; 623/26, 38

[56] References Cited

U.S. PATENT DOCUMENTS

| | | |
|---|---|---|
| 3,976,060 | 8/1976 | Hildebrandt et al. . |
| 3,977,398 | 8/1976 | Burstein . |
| 3,986,504 | 10/1976 | Avila . |
| 4,091,806 | 5/1978 | Aginsky . |
| 4,190,044 | 2/1980 | Wood . |
| 4,204,531 | 5/1980 | Aginsky . |
| 4,453,539 | 6/1984 | Raftopoulos et al. ............... 606/63 |
| 4,457,301 | 7/1984 | Walker ............................... 606/62 |
| 4,522,200 | 6/1985 | Stednitz . |
| 4,615,338 | 10/1986 | Ilizarov et al. . |
| 4,846,162 | 7/1989 | Moehring ........................... 606/64 |
| 4,854,312 | 8/1989 | Raftopoulos et al. . |
| 4,858,602 | 8/1989 | Seidel et al. ....................... 606/64 |
| 4,862,883 | 9/1989 | Freeland ............................. 606/64 |
| 4,875,474 | 10/1989 | Border . |
| 4,940,467 | 7/1990 | Tronzo . |
| 4,946,459 | 8/1990 | Bradshaw et al. . |
| 5,002,543 | 3/1991 | Bradshaw et al. ................. 606/62 |
| 5,014,719 | 5/1991 | McLeod ............................. 128/774 |
| 5,034,012 | 7/1991 | Frigg ................................. 606/62 |
| 5,034,013 | 7/1991 | Kyle et al. ......................... 606/62 |

(List continued on next page.)

FOREIGN PATENT DOCUMENTS

| | | |
|---|---|---|
| 0346247A1 | 5/1989 | European Pat. Off. . |
| 0490159A1 | 11/1991 | European Pat. Off. . |
| 2646767A1 | 5/1989 | France . |
| 4027183A1 | 8/1990 | Germany . |
| 1680127 | 9/1991 | U.S.S.R. ............................ 606/63 |
| WO94/18897 | 9/1994 | WIPO . |

OTHER PUBLICATIONS

Bliskunov, A. I., "New Methods, Rationalization and Invention" (English translation of Russian article).

J. Gotz and W. D. Schellmann, "Continuous Lengthening of the Femur by Intramedullary Stabilization", *Archiv orthopadische Unfall–Chirugie* 82:305–130 91975), copyright by J. F. Bergmann Publishing, Munich 1975. (In English and German).

(List continued on next page.)

*Primary Examiner*—Tamara L. Graysay
*Attorney, Agent, or Firm*—Hamilton, Brook, Smith & Reynolds

[57] ABSTRACT

A device for lengthening bone in a human or animal by incrementally extending the distance between discrete separated portions of the bone to permit continued bone growth between the separated portions comprising an intramedullary nail having distal and proximal portions both of which are secured within the medullar canal of the bone. A hydraulic cylinder is connected to the proximal portion and a piston is connected to the distal portion of the nail. An implantable supply of operating fluid communicates with the cylinder and ratcheting mechanism, between the piston and cylinder, limit their relative movement. A shock absorber mechanism permits limited lost motion between the piston and cylinder and ratcheting release means are employed to permit the piston and cylinder to reverse directions. Various interchangeable distal tips are disclosed to accommodate not only different bones but differently shaped medullar canals.

24 Claims, 8 Drawing Sheets

U.S. PATENT DOCUMENTS

| | | | |
|---|---|---|---|
| 5,057,103 | 10/1991 | Davis | 606/63 |
| 5,059,193 | 10/1991 | Kuslich | 606/61 |
| 5,071,435 | 12/1991 | Fuchs et al. | 623/16 |
| 5,074,882 | 12/1991 | Grammont et al. | 623/23 |
| 5,102,413 | 4/1992 | Poddar | 606/62 |
| 5,112,333 | 5/1992 | Fixel | 606/62 |
| 5,116,335 | 5/1992 | Hannon et al. | 606/62 |
| 5,122,141 | 6/1992 | Simpson et al. | 606/62 |
| 5,156,605 | 10/1992 | Pursley et al. | |
| 5,263,955 | 11/1993 | Baumgart et al. | 606/62 |

OTHER PUBLICATIONS

J. Götz und W. D. Schellmann, "Kontinuierliche Verlänerung des Femur bei intramedullärer Stabilisierung", *Arch. orthop. Unfall–Chir.* 82:305–310 (1975).

A. I. Bliskunov, "the Lengthening of the Thigh Stump by Means of Intramedullar Distractor", (English Translation of Russian Article).

BONE AND TISSUE LENGTHENING DEVICE

RELATED APPLICATIONS

This is a continuation-in-part application of copending application U.S. patent application Ser. No. 08/018,820 filed Feb. 18, 1993, now U.S. Pat. No. 5,350,379.

BACKGROUND OF THE INVENTION

This invention pertains to apparatus for extending or lengthening bones and for fracture fixation and is particularly applicable to lengthening of human bones. There are many instances where a human being has one limb, particularly a leg, which is shorter than the other which could be congenital or due to an accident.

A comminuted fracture is one in which the bone is broken into many small pieces, some in the form of splinters which overlap one another.

It has been found possible to lengthen the deformed or shortened limb or permit the comminuted fracture to heal by devices which extend a proximal portion of a bone which has been severed or splintered from a distal portion. Such devices move the distal portion of the bone away from the proximal portion in small increments. This involves extending the gap between the severed bone portions in increments of approximately ¼ mm at a time. When the bones are thus separated, new bone tissue grows in the extended gap as well as soft tissue surrounding the bone. It is possible to lengthen a bone such as a femur 10 or more centimeters over a period of a few months.

One such device was developed in the USSR by Gavriil A. Ilizarov et al. which essentially is an extendable cage which fits externally around a limb. The distal end of the cage is incrementally extended from the proximal portion mechanically. One of the problems with this type of device is that a plurality of pins are inserted through the muscle of the limb, and into both portions of the bone. With the proximal portion of the limb "anchored" by the pins in the cage, force is transmitted through the pins to pull the distal portion away from the anchored portion. Such a device is described in U.S. Pat. No. 4,615,338. One of the problems created by this type of device is that numerous incisions are created in a limb by the pins which are susceptible to infection and that the pins are continually pulling on the flesh. Another disadvantage is that the wearing of a cage over a period of months severely limits the mobility of the patient.

Numerous other devices employ an elongated rod or nail known as an intramedullary rod or nail. Such devices are inserted into the marrow cavity or medullary passage of the bone. These rods are often threaded and are anchored to the bone from within the medullar canal and are incrementally moved by nuts or ratchet means to incrementally continue separating bone portions. One such early device is shown in U.S. Pat. No. 3,986,504 to Avila. The ratcheting or extending of the threaded rod is accomplished externally by ratcheting mechanism or wrenches. Again, this type of device lends itself to infection.

Other types of devices have been developed also in the USSR by Alexander Bliskunov and employ ratcheting devices which are implanted internally and are operated by the patient himself who moves portions of his body to activate the ratcheting mechanism. One problem with this type of device is that accidental movement or excessive movement can cause too much bone separation, disturbing the growth pattern. It is to these problems that the present invention is directed. Another objective is to provide a completely implantable, hydraulically operated mechanism with as little opportunity for infection as possible and which is substantially foolproof in operation.

At least one hydraulically operated device has been discovered by Götz and Schellmann, "Continuous Lengthening of the Femur by Intramedullary Stabilization", *Archiv. orthopädische Unfall-Chirugie* 82:305–310, J. F. Bergmann Publishing, Munich (1975).

SUMMARY OF THE INVENTION

A device for lengthening bone and tissue in a human or animal is disclosed for incrementally extending the distance between discrete separated portions of the bone to permit continued growth between the separated portions. It includes an intramedullary nail having a distal portion and a proximal portion. The proximal portion of the nail is secured within the intramedullary canal of the bone at the proximal end thereof and the distal portion of the nail is secured within the intramedullary canal at the distal end thereof. A hydraulic cylinder is connected to the proximal portion and a piston moveable in the cylinder is connected to the distal end of the nail. There is a supply of operating fluid in communication with the cylinder which may be implantable or external and ratcheting mechanism is located between the proximal and distal portions of the nail, i.e., the piston and cylinder, to limit their relative movement to one direction.

An alternative ratcheting mechanism, however, permits the proximal and distal portions of the nail (i.e., piston and cylinder) to reverse directions when the pressure of the operating fluid is released.

A shock absorbing member is interposed between the piston and the cylinder and cooperates with lost motion mechanism to provide a small amount of buffered lost motion, creating an environment to enhance growth between the separated portions.

The pressurizable fluid is contained in a reservoir which may also be implantable or external and pumped either manually or from an external signalling device or an internal pump controlled by an implantable battery operated microprocessor.

The distal portion of the nail may be made as removable tips of varying configurations. They may be secured, as by screw coupling, directly to the distal portion of the nail or an elastomeric flexible coupling may be interposed between the distal portion of the nail and the discrete tip.

The tips may be slotted as from their free end toward their distal portion to give the surgeon a degree of freedom as to where he drills the bone for the screw.

The tips may be either straight or arcuate depending upon the shape of the medullar canal into which it is to be inserted. A special tibulanail is disclosed. It has an articulated distal tip.

There may be more than one bores or holes passing transversely through the tips to permit the use of more than one screw to secure it firmly to the bone.

A slot may be formed in the tip which does not extend out of the tip end also to permit the surgeon a degree of freedom when drilling the hole for the securing screw.

The tip may be provided with a pair of feet pivoted on the tip in slots. They are normally urged outwardly from the slots by compression springs such that when they are inserted into the distal end of the bone the feet engage the interior of the medullar canal locking the tip in place. On insertion, the feet would be held in the slots by a removable band.

It will be understood that the device, while illustrated as lengthening the femur, can with simple modification be adjusted to lengthen generally elongated long bones.

The above and other features of the invention, including various and novel details of construction and combinations of parts will now be more particularly described with reference to the accompanying drawings and pointed out in the claims. It will be understood that the particular bone and tissue lengthening device embodying the invention is shown by way of illustration only and not as a limitation of the invention. The principles and features of this invention may be employed in varied and numerous embodiments without departing from the scope of the invention.

DETAILED DESCRIPTION OF THE INVENTION

Figure 1:
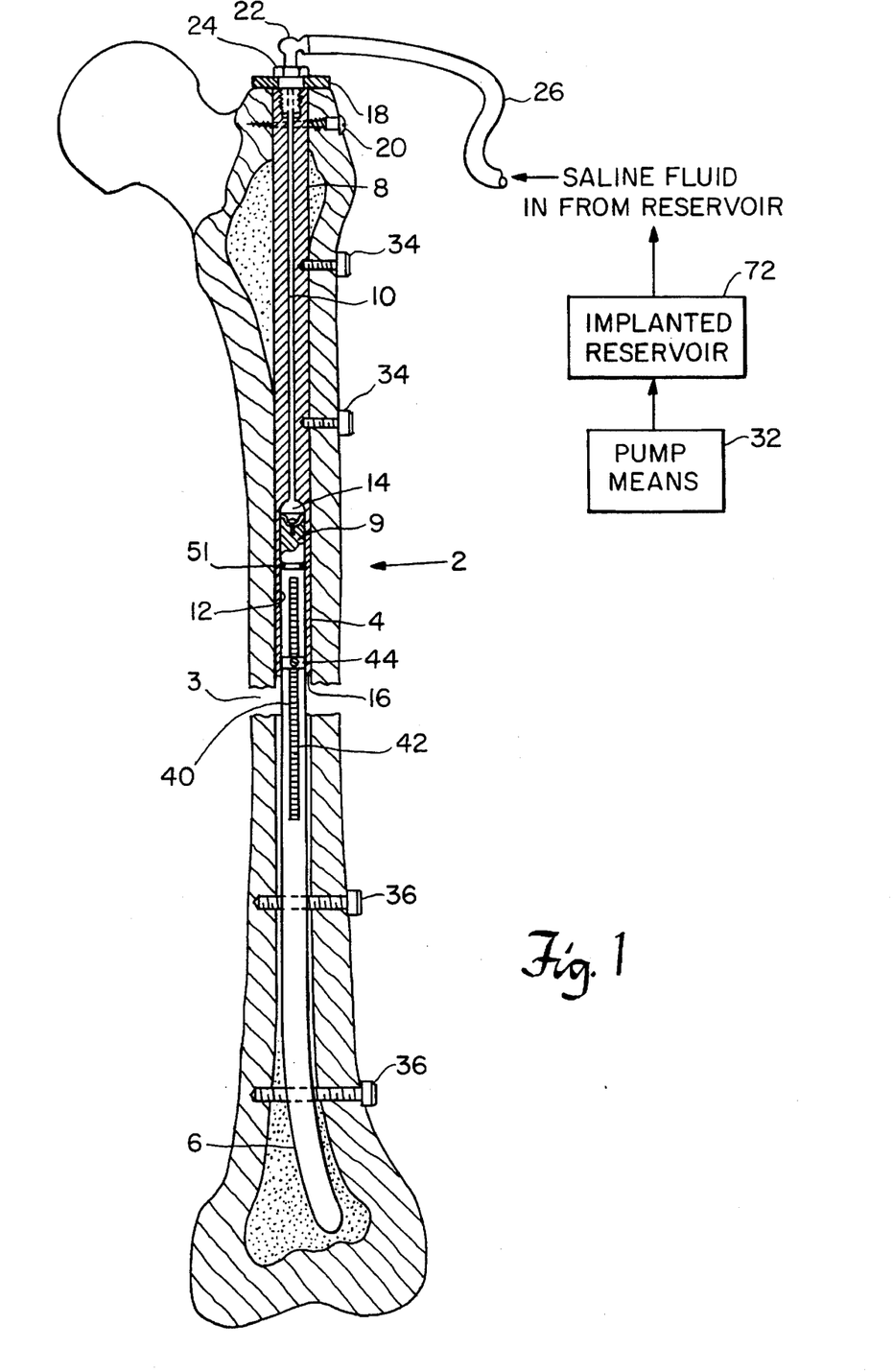
FIG. 1 is a sectional view of a bone lengthening device embodying the present invention and which is located in the femur.

A device for lengthening bone and soft tissue in a human or other animal by incrementally extending the distance between discrete separated portions of the bone or tissue to permit continued growth between the portions will be seen in FIG. 1. The device is shown inserted into a human femur 2, although it could be another bone in a human or animal. Initially, a surgeon removes the soft, pulpy material in the medullar canal to produce an elongate opening. He then cuts the bone transversely as at gap 3 to receive an intramedullary nail or rod generally designated 4.

The rod includes a distal portion 6 and a proximal portion 8. The proximal portion has formed in it a central bore 10 which leads to a cylinder 12 having an upper, domed shaped, fluid chamber 14. The proximal portion terminates at a point designated 16. A plate 18 is securable by screws 20 to the femur. A one-way valve 22 is threaded into the plate 18 and/or portion 8 and is secured by a nut 24 at the proximal end of the femur. A flexible conduit 26 leads from the one-way valve 22 to an implantable reservoir 72 (FIG. 1) which, in turn, is actuated by a pump means 32, both elements to be described in greater detail hereinafter. The proximal portion 8 of the intramedullary nail is secured to the femur by screws 34. The distal portion 6 of the intramedullary nail is secured by screws 36 within the distal portion of the medullar canal and on its upper end is formed a piston 9. Ratchet teeth 40 are formed in a line 42 in the piston 9.

A collar 44 is secured to the piston 9 by screws 48 and is received within an annular groove in the cylinder 12. A dog 46 is received within a slot 49 in the collar 44 for movement inwardly and outwardly radially with regard to the piston and has teeth 50 engagable with the mating teeth 40 formed in the piston 9. A fluid tight gasket 51 is fitted in a groove in the piston 9 and engages the wall of the cylinder 12. An annular, elastomeric shock absorbing element 52 is engagable with the collar 44 and the top 55 of the annular groove.

Lost motion between the piston 9 and the cylinder 12 occurs to the extent of the gap 54 between the collar 44 and the annular groove as the patient's lower leg is moved, thus causing the lower cut portion of the femur to move or vibrate slightly relative to the upper cut portion. In other words, the piston is permitted a small amount of lost motion relative to the cylinder, buffered by the shock absorber 52, which motion or vibration is beneficial to bone growth.

Figure 3:
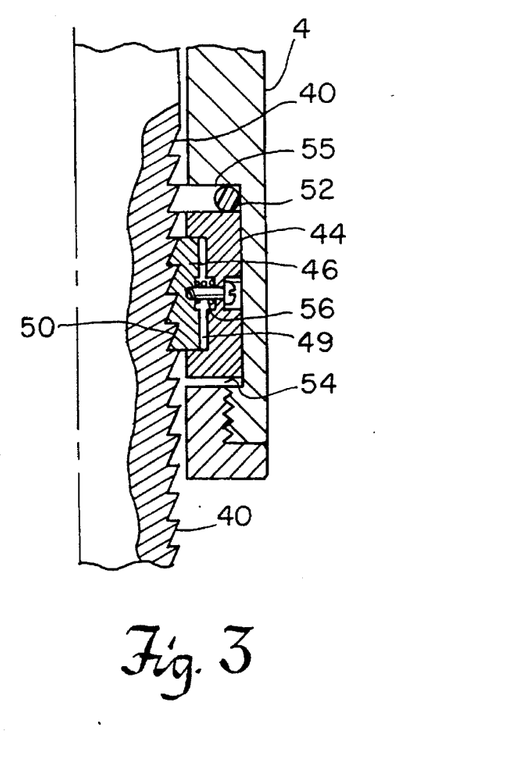
FIG. 3 is a detailed sectional view on an enlarged scale taken on the lines III—III of FIG. 2 of ratchet means for limiting movement of the device shown in FIG. 1.

The dog 46 is urged to the left as seen in FIG. 3 by a compression spring 56 which is received within the collar 44. When the piston 9 and, hence, the distal portion of the bone, is urged downwardly by pressurized fluid entering the chamber 14, the dog 46 is moved slightly to the right as viewed in FIG. 3 by the teeth 40. Each tooth moves downwardly engaging the next adjacent tooth. This limits the motion of the distal end of the nail relative to the proximal portion to one direction. Thus, the piston can only move out of the cylinder upon admission of pressurized fluid to the chamber 14 above the piston head and not reverse direction. This will be done by the surgeon when the bone growth is completed.

Figure 2:
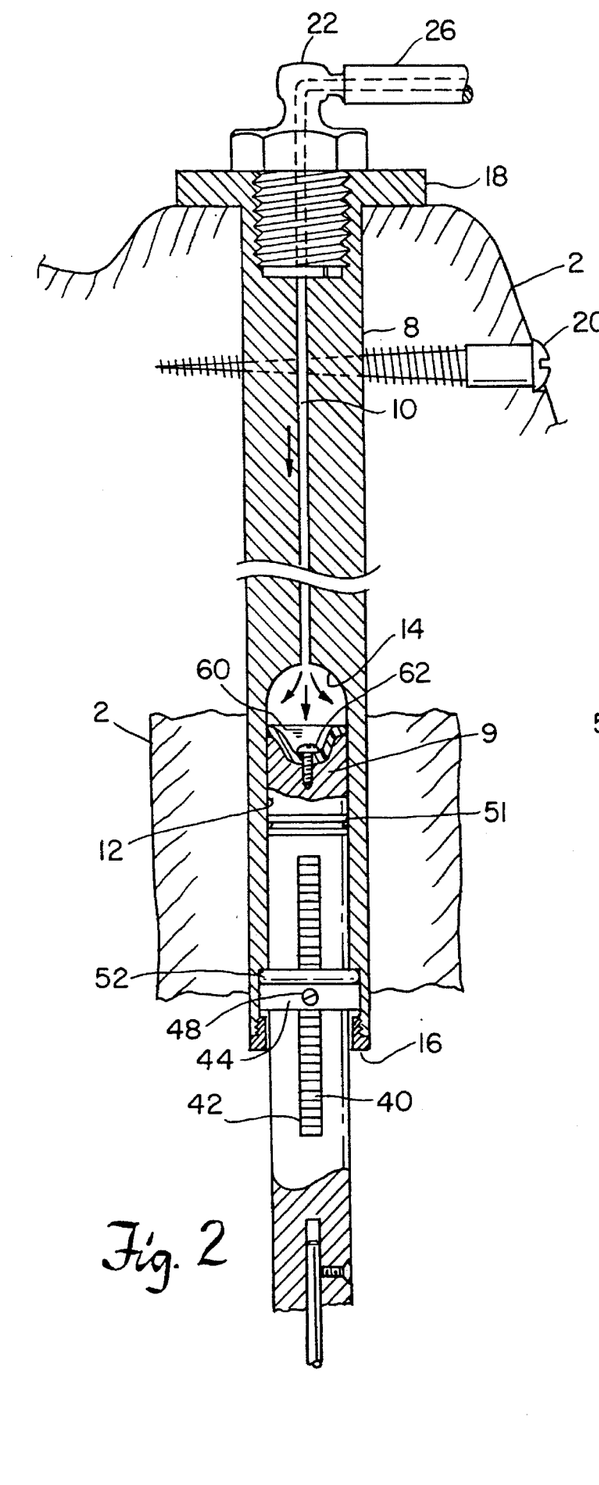
FIG. 2 is a detail view of an upper portion of the device shown in FIG. 1.

An elastomeric piston cap 60 (FIG. 2) is secured by a screw 62 to the top of the piston member 9. The edges of the cap 62 maintain a seal against the inner wall 64 of the cylinder 12 which in conjunction with the annular seal 51 assures that there is no leakage of the saline operating fluid.

Whereas the invention contemplates either an external or internal supply of operating fluid and either an external or internal pump, the internal or implantable version is the preferred embodiment.

Figure 7:
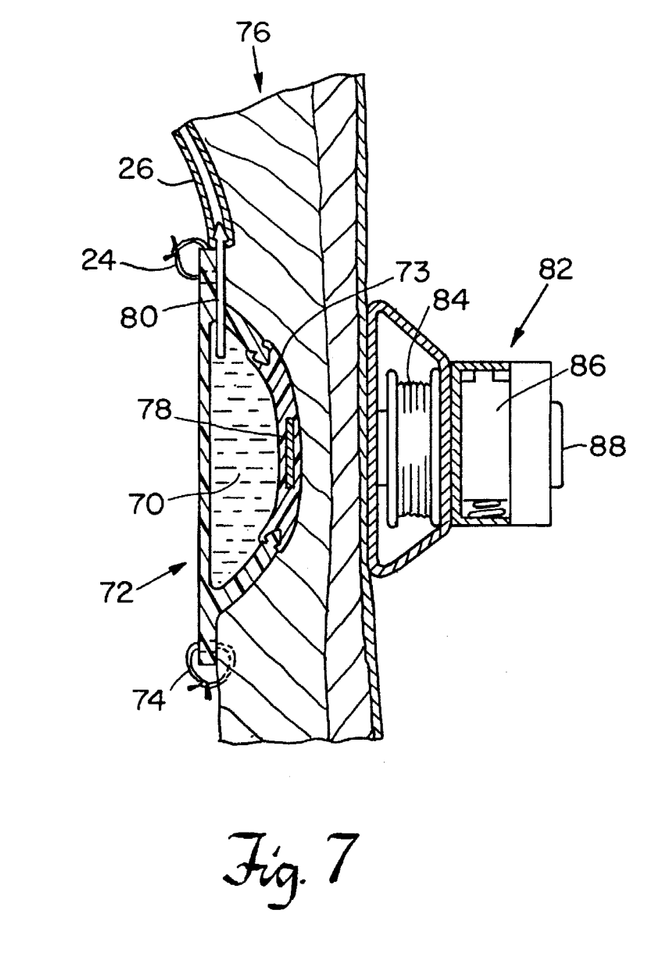
FIG. 7 is a detail view of means for supplying pressurized operating fluid to the device.

Pump means 32 and reservoir 72 will now be described referring next to FIG. 7. There will be seen an implantable supply of saline operating fluid 70 contained within an elastomeric diaphragm reservoir 72, implanted and secured by sutures 74 on an inner portion of the skin and muscle of the patient generally indicated 76. A ferromagnetic disk 78 is secured in an upper domed portion 73 of the diaphragm reservoir. The implanted conduit 26 which leads to the one-way valve 22 of the cylinder communicates with an opening 80 in the fluid reservoir 72.

An external pump exciting member 82 is engagable with the skin adjacent the ferromagnetic disk 78. It comprises an electromagnet 84, a battery 86 and a trigger 88 such that a surgeon or even a patient can trigger the exciting member to cause the ferromagnetic disk 78 to pulse toward and away from the electromagnet 84 to compress and relax the diaphragm reservoir to cause the saline fluid to pass through the conduit 26 through the one-way valve 22 and into the domed chamber 14 at the top of the piston.

Figure 8:
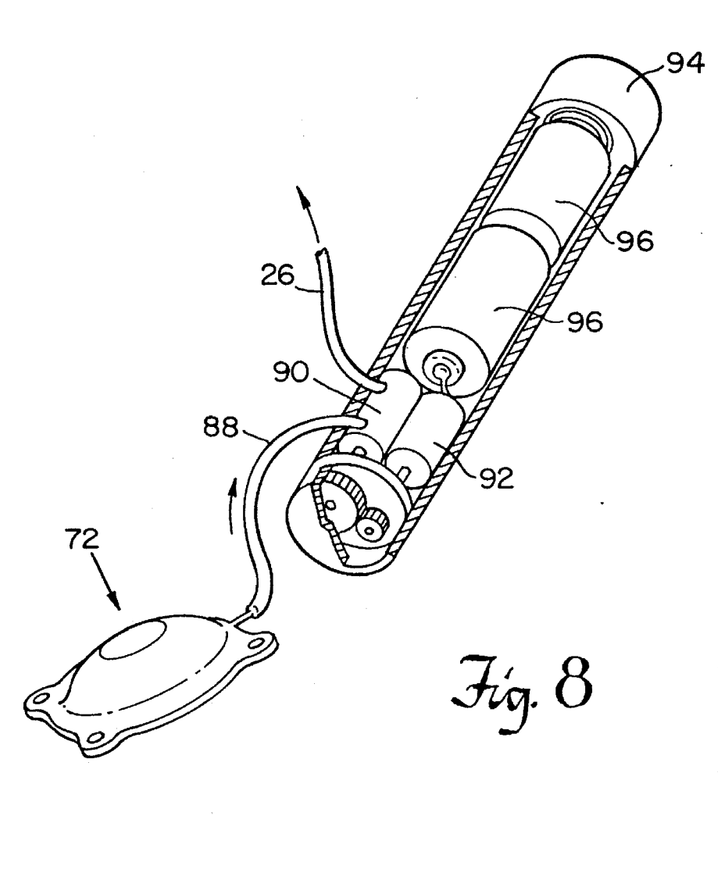
FIG. 8 is an alternative embodiment of the means for supplying pressurized operating fluid.

An alterative pump means 32a and reservoir 72a is shown in FIG. 8. The reservoir 72a is connected by a flexible conduit 26a to a pump 90 operated from a reversible geared motor 92. A programmable microprocessor 94, through batteries 96, supplies signal to the motor 92 to pump fluid from the reservoir 72a through the conduit 26b into the upper domed chamber 14 of the cylinder 12. The motor 92, being reversible, may also pump fluid back to the reservoir 72a.

Figure 4:
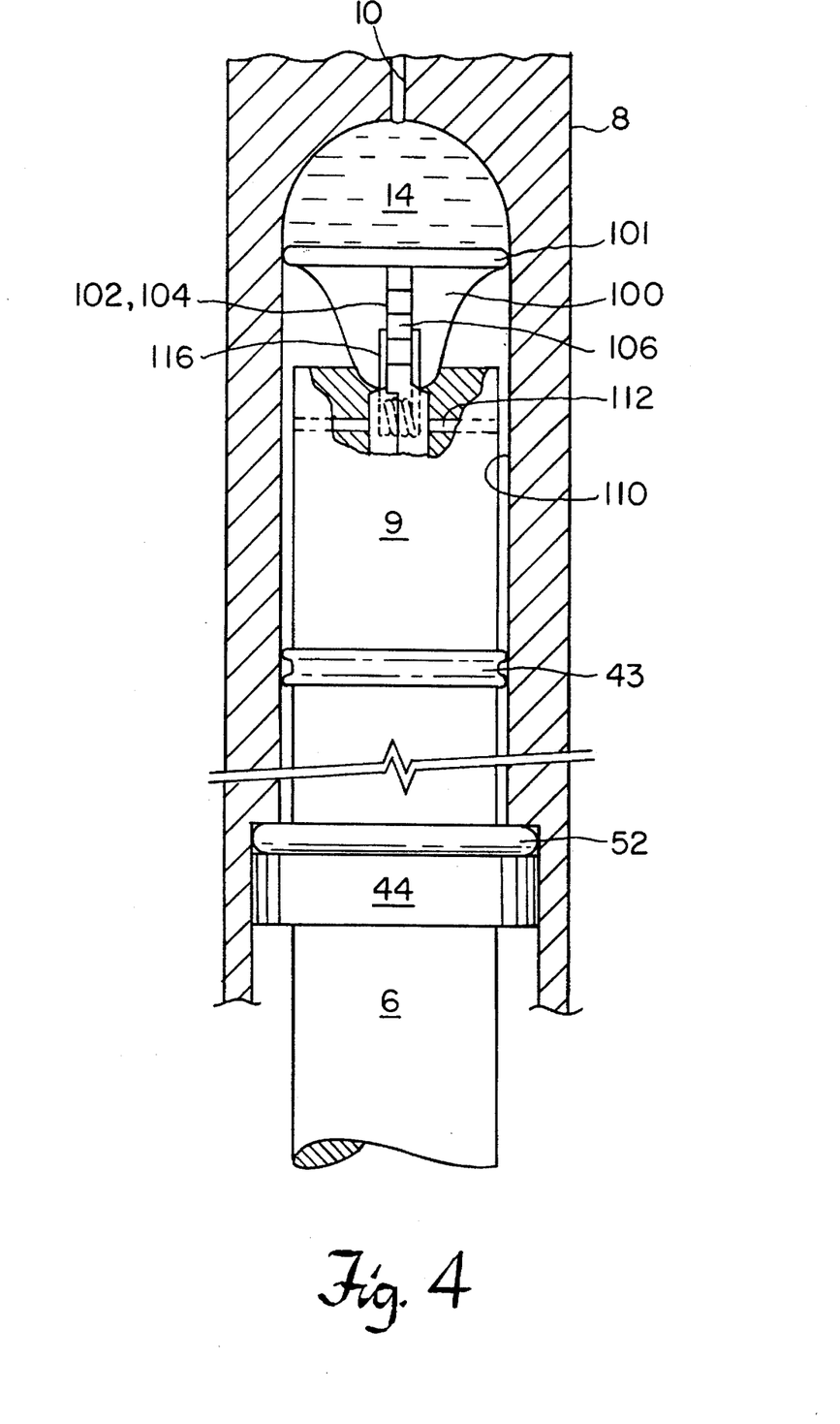
FIGS. 4, 5 and 6 are detailed enlarged views of an alternative embodiment of the ratcheting mechanism including means for reversing the direction of the mechanism.
Figure 5:
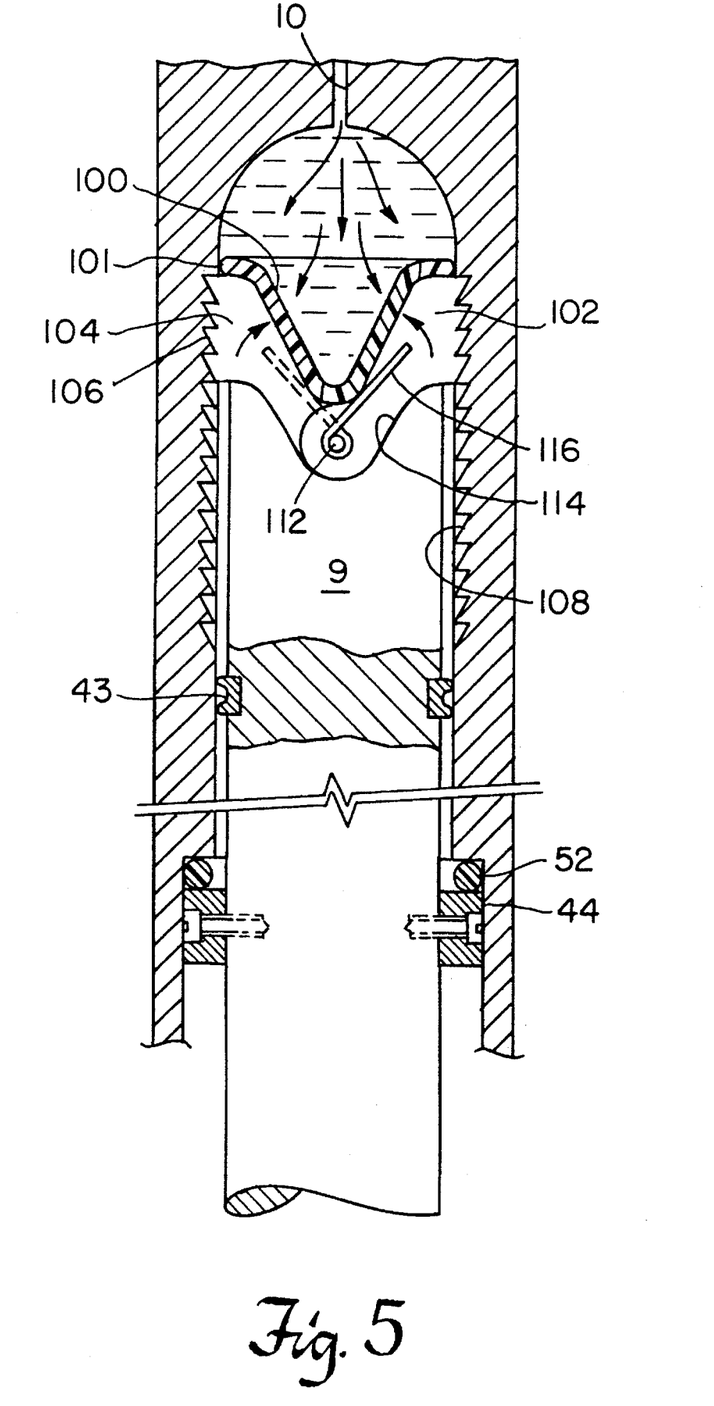
Figure 6:
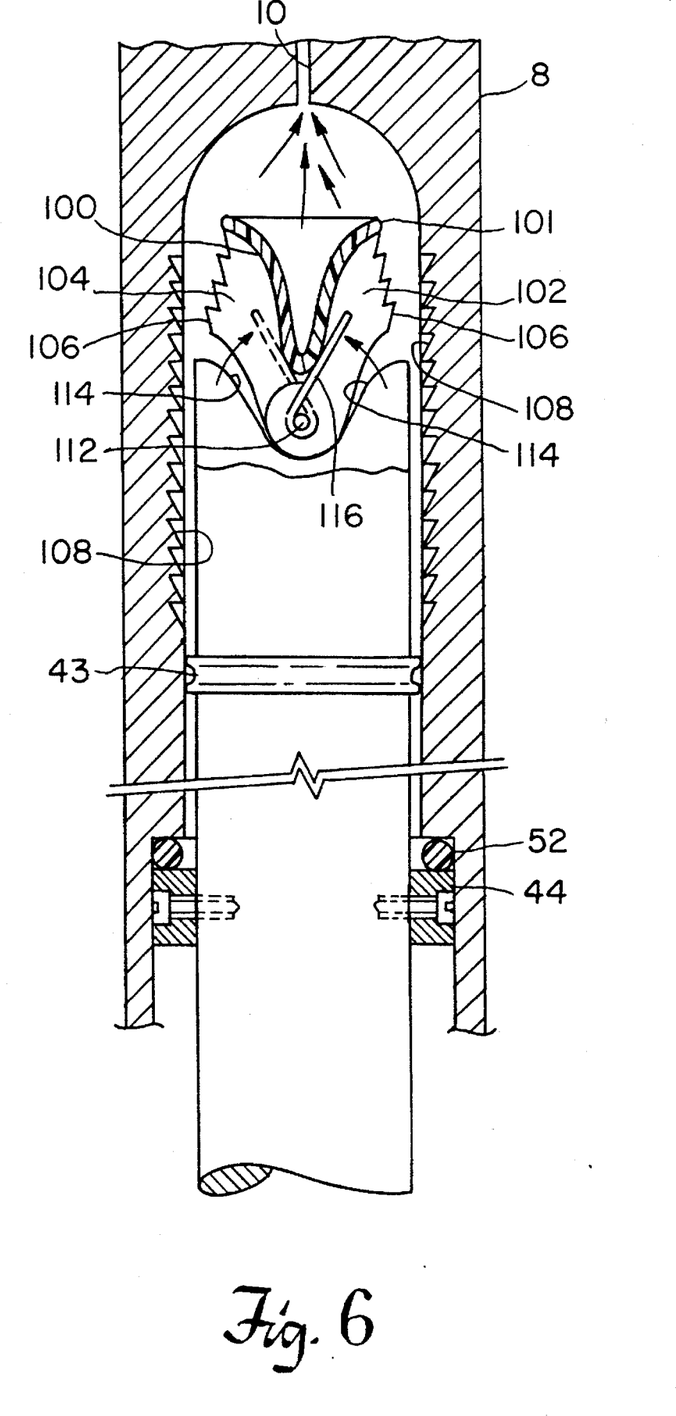

With reference to FIGS. 4, 5 and 6, mechanism for reversing the direction of the piston 9a within the cylinder will now be described. At the top of the piston, an inverted, bell shaped seal 100 is provided which is mounted for flexure between a pair of hinged ratcheting wings 102, 104, having teeth 106 which are engagable with mating teeth 108 on the interior of the cylinder wall. The wings 102, 104 are pivoted on a rod 112 received within bores in the top of the piston 9a. The piston is cut away at 114 to accommodate the lower ends of the wings which pivot inwardly and outwardly under the control of a coiled spring 116.

When it is desired to incrementally separate the proximal and distal portions of the bone, the implantable reservoir 72 is pressurized either externally by the electromagnet 82 or, preferably, the reservoir 72a is pressurized by the microprocessor operated pump 90 because the system is reversible. This causes fluid to flow through the flexible tube 26 through the passageway 10 into the upper domed chamber 14 of the cylinder. The pressurized fluid acts against the seal 100 expanding its upper annular portion 101 to expand against the cylinder walls as shown in FIGS. 4 and 5. The pressure urges the wings 102, 104 apart against the force of its spring 116. The teeth 106 engage the teeth 108 in the cylinder walls, one by one. Continued pressurization urges the piston 9a downwardly causing the bones to separate and permit new growth to take place.

If, for some reason, the bone portions have been separated too much or it is desired to terminate the bone growth, depressurization of the fluid above the piston permits the coiled spring 116 to squeeze the seal 100 together as shown in FIG. 6 with the pressurized saline fluid reversing direction in the passageway 10 and returning to the reservoir 72a. The reversible pump 90 controls the fluid reversal.

Without using the pump 90, with the teeth 106 on the wings 102, 104 withdrawn from the teeth 108 on the inner cylinder walls, pressure on the distal end of the bone, as for example, by the orthopedist applying counter pressure, can cause the piston 9a and the distal end of the bone to rise slightly, closing the gap 3 between it and the proximal portion of the bone.

A plurality of distal tips and adaptors will now be described.

Whereas the distal portion or tip 6 of the intermedullary nail or rod 4 has been shown as one piece, the distal end may be removable to include alternative distal tips.

Figure 9:
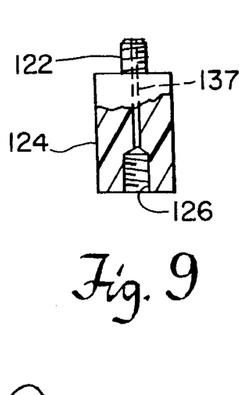
FIG. 9 is a threaded coupler for releasably joining selected distal tips to the piston.
Figure 14:
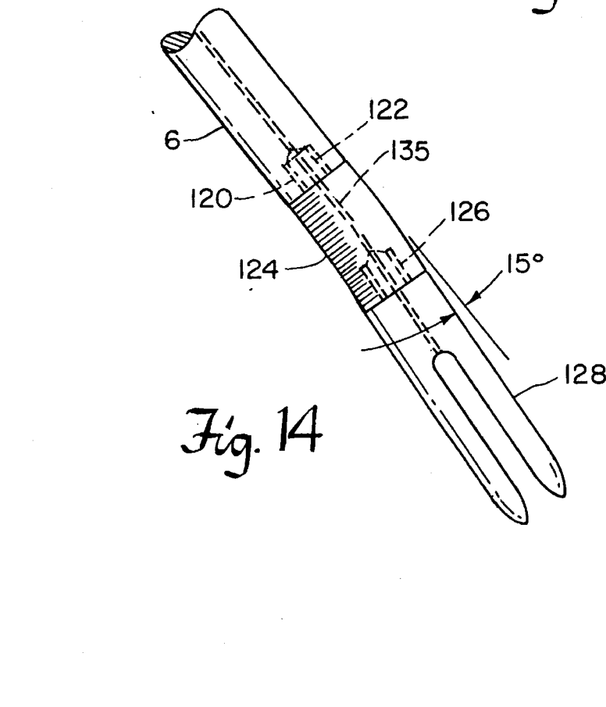
FIG. 14 is a view of the tip of FIG. 10 joined by the coupler to the piston.

FIG. 14 shows the distal portion 6 having a female threaded portion 120 which receives the male threaded portion 122 of a coupler 124 which is also shown in FIG. 9. Axially opposite the male threaded portion 122 is a female threaded portion 126.

The coupler of FIG. 9 is shown as being an elastomeric material for flexibility and is made of any appropriate bio-compatible material.

FIGS. 10–13 show a plurality of replaceable distal tips 128 to 134. Tip 128 is cylindrical and has an elongated slot 136 extending axially. Tip 130 is also cylindrical having a spherical nose 138 and an elongate slot 140 running axially terminating short of the nose 138. Tip 132 is cylindrical having a transverse bore 143. Tip 134 is arcuate but has a cylindrical cross-section and a cylindrical transverse bore 144.

The purposes of the slots 136 and 140 are to permit the hole in the bone at its distal end to be drilled transversely to receive the pin 36 (FIG. 1) without precise location lengthwise of this bone. The elongate slots 136 and 140 being able to accommodate the screw or the pin 36 at a point along their lengths.

Figures 10, 11, 12:
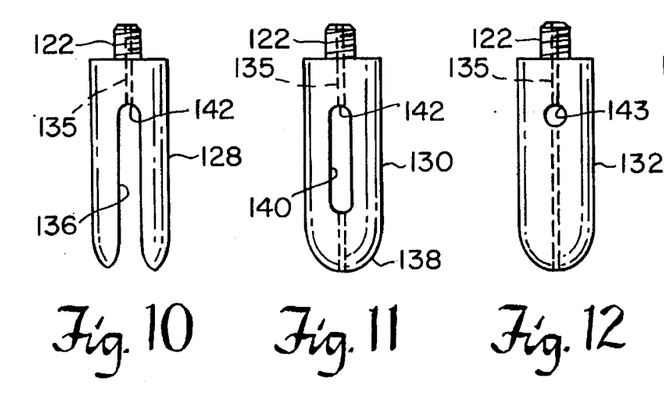
FIGS. 10 through 13 are alternative distal tips for use with the device.

The additional purposes of the slotted tips as in FIGS. 10 and 11 are such that when the piston is being urged toward the distal portion of the bone, i.e. away from the proximal portion, the pin 36 (FIG. 1) abuts the upper ends 142 of either of the slots 136, 140. Lost motion provided by the element 52 then comes into play. The slots 136, 140 readily accommodates the reverse motion by causing the ends 142 of the slots 136, 140 to move away from the pin 36 which is fixed in the bone. In addition, the slotted tip 128 can be removed without removal of the pin 36. By use of the tips of the embodiment of FIGS. 10 and 11, the vibratory effect or the shock-absorbing effect of the element 51 is negated. Whereas, with the tips of FIGS. 12 and 13, the pin 36 fits directly and firmly into the bores 143 or 144 would cause the tip to reciprocate.

Figure 13:
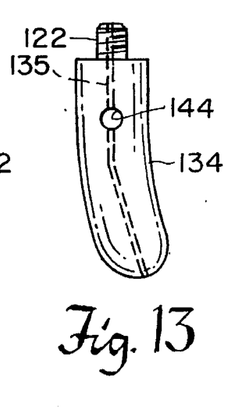

The arcuate configuration of the tip shown in FIG. 13 is to fit within the enlarged intermedullary cavity in the bone shown at the lower portion of FIG. 1.

The axial passageways 135 are located in the tips to aid the surgeon in removing the tips should they become inadvertently lodged in the bond by the use of a "fishing wire."

Figure 15:
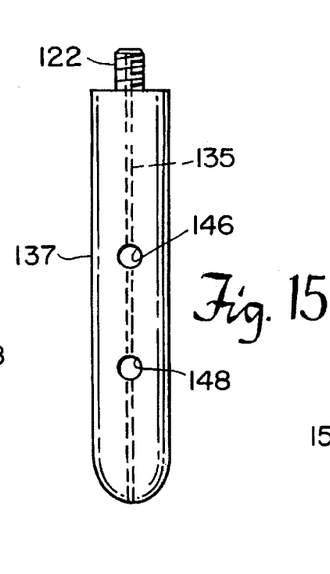
FIG. 15 is another alternative distal tip.

FIG. 15 discloses a somewhat longer tip 137 having two transverse bores 146 and 148 for receiving two pins or screws 36.

Figure 16:
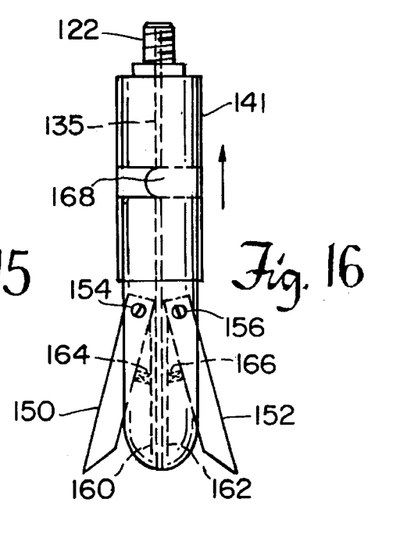
FIG. 16 is still another alternative distal tip.

FIG. 16 discloses yet another embodiment of another removable tip 141 which does not require the bone to be drilled to receive the locking pin 36. A pair of feet 150, 152 are pivoted at 154 and 156 in slots 160, 162. They are urged outwardly from the slots by compression springs 164, 166 such that when they are inserted into the distal end of the bone the feet engage the interior of the medullar canal locking the tip in place. On inserting the tip 140, the feet are held in place by a removable band 168 which may be either removed or slid upwardly by the surgeon to permit the feet to be biased into the locking position.

Figure 17:
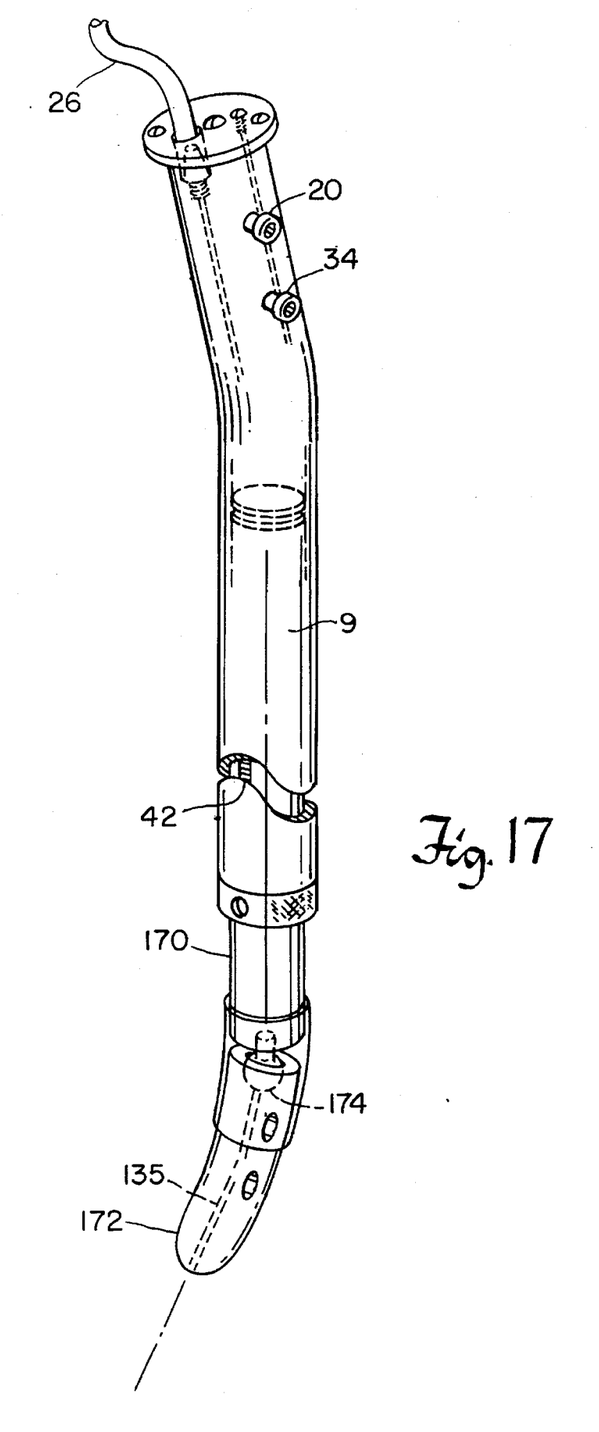
FIG. 17 is an articulated tibial nail.

FIG. 17 discloses a device which is usable in fixating or extending the length of the tibia. As with the FIG. 1 device, the tibial nail includes a piston 9, screws 20 and 34, flexible conduit 26, ratcheting mechanism 42, all functioning as in the FIG. 1 embodiment. The lower end 170 of the piston is removable as is the coupling device disclosed in FIG. 9. The distal tip 172 is articulable relative to the piston 9 by way of a ball and socket joint 174 joining the tip 172 to the lower end 170 of the piston. This is to facilitate entry of the nail into the tibia because of its unique shape.

What is claimed is:

1. A device for lengthening bone and tissue and for fracture fixation in a human or animal by incrementally extending the distance between discrete separated portions of the bone to permit continued growth between the separated portions comprising:

an intramedullary nail having a distal portion and a proximal portion;

the proximal portion of the nail being securable within the medullar canal of the bone at the proximal end of the bone;

the distal portion of the nail being securable within the medullar canal of the bone at the distal end of the bone;

a hydraulic cylinder connected to the proximal portion of the nail;

a piston connected to the distal portion of the nail and movable in the cylinder;

a supply of implantable operating fluid in communication with the cylinder;

ratcheting mechanism between the piston and cylinder to limit their relative movement and that of the bone portions to which they are secured to one direction; and a removable slotted tip and releasable securing means for securing the tip to the distal portion of the nail.

2. A device according to claim 1 further comprising a pump in communication with the implantable supply of operating fluid to pump the operating fluid.

3. A device according to claim 1 wherein the releasable securing means is a flexible coupling.

4. A device according to claim 1 wherein the removable tip has spring biased feet for engaging the medullar canal.

5. A device according to claim 1 wherein the releasable securing means is articulable.

6. A device for lengthening bone and tissue and for fracture fixation in a human or animal by incrementally extending the distance between discrete separated portions of the bone to permit continued growth between the separated portions comprising:

an intramedullary nail having a distal portion and a proximal portion;

the proximal portion of the nail being securable within the medullar canal of the bone at the proximal end of the bone;

the distal portion of the nail being securable within the medullar canal of the bone at the distal end of the bone;

a hydraulic cylinder connected to the proximal portion of the nail;

a piston connected to the distal portion of the nail and movable in the cylinder;

a supply of implantable operating fluid in communication with the cylinder;

a shock absorbing element operatively engagable with both the piston and the cylinder;

means to permit limited lost motion between the piston and the cylinder against the shock absorbing element in the direction of movement of the piston to stimulate bone growth between the separated portions of the bone; and a removable slotted tip and releasable securing means for securing the tip to the distal portion of the nail.

7. A device according to claim 6 further comprising a pump in communication with the implantable supply of operating fluid to pump the operating fluid.

8. A device according to claim 6 wherein the releasable securing means is a flexible coupling.

9. A device according to claim 6 wherein the removable tip has spring biased feet for engaging the medullar canal.

10. A device according to claim 6 wherein the releasable securing means is articulable.

11. A device for lengthening bone and tissue and for fracture fixation in a human or animal by incrementally extending the distance between discrete separated portions of the bone to permit continued growth between the separated portions comprising:

an intramedullary nail having a distal portion and a proximal portion;

the proximal portion of the nail being securable within the medullar canal of the bone at the proximal end of the bone;

the distal portion of the nail being securable within the medullar canal of the bone at the distal end of the bone;

a hydraulic cylinder connected to the proximal portion of the nail;

a piston connected to the distal portion of the nail and movable in the cylinder;

a supply of implantable operating fluid in communication with the cylinder;

ratcheting mechanism between the piston and cylinder to limit their relative movement and that of the bone portions to which they are secured to one direction;

mechanism to permit the piston to reverse directions relative to the cylinder when the pressure of the operating fluid is released; and a removable slotted tip and releasable securing means for securing the tip to the distal portion of the nail.

12. A device according to claim 11 further comprising a pump in communication with the implantable supply of operating fluid to pump the operating fluid.

13. A device according to claim 11 wherein the releasable securing means is a flexible coupling.

14. A device according to claim 11 wherein the removable tip has spring biased feet for engaging the medullar canal.

15. A device according to claim 11 wherein the releasable securing means is articulable.

16. A device for the fixation of a bone in a human or animal, which bone is fractured and separated into a distal end and a proximal end, the device comprising:

a distal elongate member being securable within the medullary canal of the bone at the distal end of the bone;

a proximal elongate member being securable within the medullary canal of the bone at the proximal end of the bone;

a coupling mating the distal and proximal members to form an intramedullary nail having a maximum length which permits relative longitudinal motion between the distal and proximal members, the coupling being responsive to longitudinal compression to shorten the length of the formed nail; and a buffering member disposed within the coupling between the distal and proximal members to permit lost motion to take place between the distal and proximal members, thereby facilitating continued growth between the separated portions of the bone.

17. A device according to claim 16 wherein the buffering member is a shock absorber.

18. A device according to claim 16 wherein the buffering member is elastomeric.

19. A device according to claim 16 wherein the buffering member includes an annular ring of an elastomeric material.

20. A device according to claim 16 having a removable tip securable to the distal elongate member.

21. A device according to claim 16 having a removable tip and a flexible coupling joining the removable tip to the distal elongate member.

22. A device according to claim 16 having a removable slotted tip securable to the distal elongate member.

23. A device according to claim 16 having a removable tip with spring biased feet for engaging the medullar canal, the tip being securable to the distal elongate member.

24. A device according to claim 16 having a removable tip and articulable means for joining the tip to the distal elongate member.

* * * * *